United States Patent
Wynn et al.

(10) Patent No.: US 8,066,970 B2
(45) Date of Patent: *Nov. 29, 2011

(54) CONTRAST AGENTS

(75) Inventors: Duncan Wynn, Amersham (GB); Gareth Humphries, Amersham (GB)

(73) Assignee: GE Healthcare AS, Oslo (NO)

( * ) Notice: Subject to any disclaimer, the term of this patent is extended or adjusted under 35 U.S.C. 154(b) by 1209 days.

This patent is subject to a terminal disclaimer.

(21) Appl. No.: 11/746,720

(22) Filed: May 10, 2007

(65) Prior Publication Data

US 2007/0264201 A1 Nov. 15, 2007

(30) Foreign Application Priority Data

May 11, 2006 (NO) .................................. 20062120

(51) Int. Cl.
- *A61K 51/00* (2006.01)
- *A61M 36/14* (2006.01)
- *A61B 5/00* (2006.01)
- *A61B 8/00* (2006.01)
- *A61B 10/00* (2006.01)

(52) U.S. Cl. .......................... 424/1.11; 424/1.65; 424/9.6

(58) Field of Classification Search .................... 424/9.6, 424/1.65

See application file for complete search history.

(56) References Cited

U.S. PATENT DOCUMENTS 5,866,100 A * 2/1999 Tournier et al. ............ 424/9.452

* cited by examiner

*Primary Examiner* — Michael G Hartley
*Assistant Examiner* — Melissa Perreira

(57) ABSTRACT

The present invention relates to a class of compounds and to diagnostic compositions containing such compounds where the compounds are iodine containing compounds. More specifically the iodine containing compounds are chemical compounds containing an aliphatic central moiety containing hydroxyl groups allowing for the arrangement of three iodinated phenyl groups bound thereto.

The invention also relates to methods employing such diagnostic compositions as contrast agents in diagnostic imaging and in particular in X-ray imaging and to contrast media containing such compounds.

22 Claims, No Drawings

CONTRAST AGENTS

TECHNICAL FIELD OF THE INVENTION

The present invention relates to a class of compounds and to diagnostic compositions containing such compounds where the compounds are iodine containing compounds. More specifically the iodine containing compounds are chemical compounds containing an aliphatic central moiety containing hydroxyl groups allowing for the arrangement of three iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds, is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose.

SUMMARY OF THE INVENTION

The present invention provides contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a central aliphatic moiety, allowing for the arrangement of three iodinated phenyl groups bound to thereto through linker groups. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

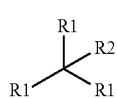

Formula (I)

wherein
each $R^1$ independently are the same or different and denote a moiety —CHOH—CHOH—CO—$NR^3$—R;
$R^2$ denote hydrogen and $C_1$-$C_4$ alkyl where the alkyl group may be substituted by hydroxyl and amino groups and interrupted by an oxygen atom;
each $R^3$ independently are the same or different and denote a hydrogen atom and an acyl group
each R independently are the same or different and denote a triiodinated phenyl group, preferably a 2,4,6-triiodinated phenyl group further substituted by two groups $R^4$ wherein each $R^4$ are the same or different and denote a hydrogen atom or a non-ionic hydrophilic moiety, provided that at least one $R^4$ group in the compound of formula (I) is a hydrophilic moiety;
and salts or optical active isomers thereof.

The substituent $R^2$ should preferably be a hydrogen atom or a methyl group, and most preferably should denote hydrogen.

$R^3$ preferably denotes a hydrogen atom and aliphatic organic acid residue, preferably a $C_2$ to $C_5$ organic acid such as formyl, acetyl, propionyl, butyryl, isobutyryl and valeriyl moieties. Hydroxylated acyl moieties are also feasible. More preferred are hydrogen and acetyl groups, and preferably all $R^3$ in formula (I) are the same. Most preferred all substituents $R^3$ in formula (I) are the same and denote hydrogen.

Each of the iodinated R group should be the same or different and preferably denote a 2,4,6-triiodinated phenyl group, further substituted by two groups $R^4$ in the remaining 3 and 5 positions in the phenyl moiety.

The non-ionic hydrophilic moieties may be any of the non-ionizing groups conventionally used to enhance water solubility. Hence, the $R^4$ substituents may be the same or different and shall preferably all denote a non-ionic hydrophilic moiety comprising esters, amides and amine moieties, that optionally are further substituted by a straight chain or branched chain $C_{1-10}$ alkyl groups, preferably $C_{1-5}$ alkyl groups, and optionally additionally with one or more $CH_2$ or CH moieties replaced by oxygen or nitrogen atoms. The $R^4$ substituents may also further contain one or more groups selected from oxo, hydroxyl, amino or carboxyl derivative, and oxo substituted sulphur and phosphorus atoms. Each of the straight or branched alkyl groups are preferably containing 1 to 6 hydroxy groups and more preferably 1 to 3 hydroxy groups. Therefore, in a further preferred aspect, the $R^4$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or carbamoyl linkage.

The $R^4$ groups of the formulas listed below are particularly preferred:
—CONH—$CH_2$—$CH_2OH$
—CONH—$CH_2$—CHOH—$CH_2OH$
—CON($CH_3$)$CH_2$—CHOH—$CH_2OH$
—CONH—CH—($CH_2OH$)$_2$
—CON—($CH_2$—$CH_2OH$)$_2$
—CON—($CH_2$—CHOH—$CH_2OH$)$_2$
—$CONH_2$
—$CONHCH_3$
—$NHCOCH_2OH$
—N($COCH_3$)H
—N($COCH_3$) $C_{1-3}$ alkyl
—N($COCH_3$)-mono, bis or tris-hydroxy $C_{1-4}$ alkyl
—N($COCH_2OH$)-hydrogen, mono, bis or tris-hydroxy $C_{1-4}$ alkyl
—N(CO—CHOH—$CH_2OH$)-hydrogen, mono, bis or trihydroxylated $C_{1-4}$ alkyl
—N(CO—CHOH—CHOH—$CH_2OH$)-hydrogen, mono, bis or trihydroxylated $C_{1-4}$ alkyl
—N($COCH_2OH$)$_2$
—CON($CH_2$—CHOH—$CH_2OH$)($CH_2$—$CH_2OH$)
—CONH—C($CH_2OH$)$_3$ and
—CONH—CH($CH_2$—OH)(CHOH—$CH_2OH$).

Still more preferably the $R^4$ groups will be equal or different and denote one or more moieties of the formulas —CONH—$CH_2$—CHOH—$CH_2OH$, —CONH—CH—($CH_2OH$)$_2$, —CON—($CH_2$—$CH_2OH$)$_2$, —CON—($CH_2$—CHOH—$CH_2OH$)$_2$, —CON($CH_3$)$CH_2$—CHOH—$CH_2OH$, —$NHCOCH_2OH$ and —N($COCH_2OH$)-mono, bis or tris-hydroxy $C_{1-4}$ alkyl, and even more preferably all $R^4$ groups are equal and denote one of these moieties.

Most preferred all substituents $R^1$ in formula (I) are equal.

Thus, preferred structures according to the invention include the compounds of formula (II):

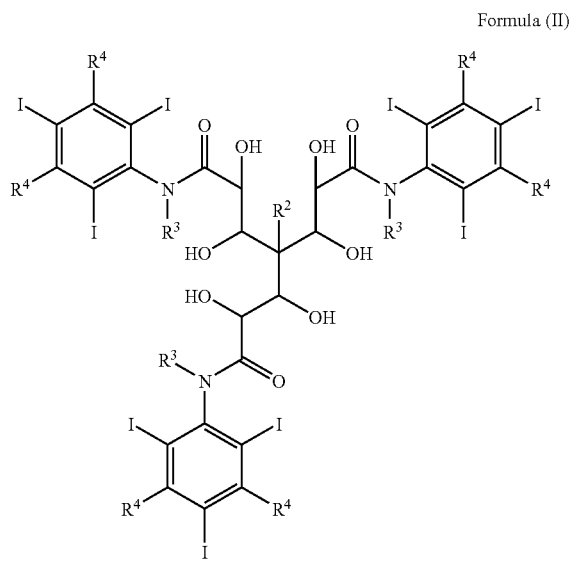

Formula (II)

In formula (II), each group $R^2$, $R^3$ and $R^4$ has the meaning above, more preferably all $R^4$ groups are the same and denote non-ionic hydrophilic moieties, the $R^3$ groups are the same and denote a hydrogen atom and the $R^2$ group denote a hydrogen atom.

In a particularly preferred example the preferred structures according to the invention include the compound of formula (III) below. In formula (III) the $R^2$ group denote a hydrogen atom, all three $R^3$ groups are hydrogen atoms and all $R^4$ are 2,4,6-triiodo-3,5-(2,3-dihydroxypropyl carbamido) phenyl residues.

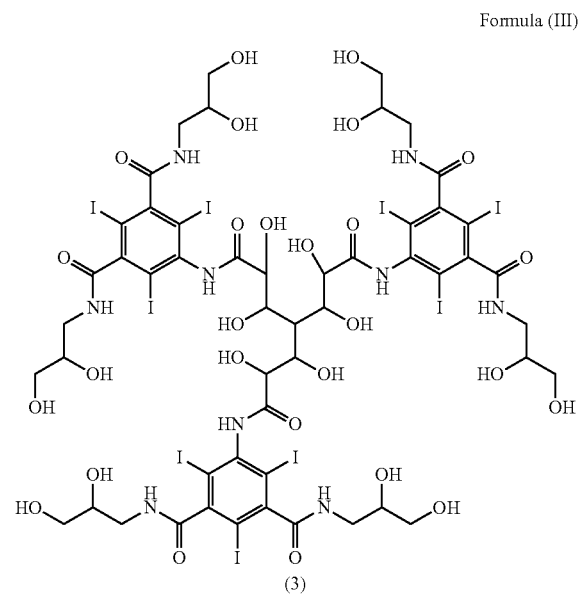

Formula (III)

(3)

The compounds of formula (I) will attain a relatively compact, folded conformation. Such conformations are relatively round and globular forms such as a star-form with the relatively bulky iodinated phenyl substituents filling up the area between the 3 arms of the star. Globular molecules will usually have enhanced solubility compared with similar molecules with a more planar structure.

At an iodine concentration of 320 mg/ml, which is a common concentration for commercially available iodinated contrast media, the concentration of the compound of formula (I) will be approximately 0.28 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

The compounds of the general formula (I) can be synthesized by multistep procedures from starting materials that are either known from the state of art or that are commercially available. Tri-iodinated phenyl groups R and precursors thereof are commercially available or can be produced following procedures described or referred to e.g. in WO95/35122 and WO98/52911. 5-amino-2,4,6-triiodo-isophtalic acid for example is available e.g. from Aldrich and 5-amino-2,4,6-triiodo-N,N'-bis(2,3-dihydroxypropyl)-isophtalamide is commercially available e.g. from Fuji Chemical Industries, Ltd. Alkyl-amines are likewise commercially available or readily synthesized from available starting materials.

To synthesize compounds of formula (I), the $R^4$ groups or precursors thereof denoted $R^{4'}$ on the R group are protected and a reactive substituent is formed that is brought to react with an alkyl-triamine. Suitable, the reactive functionality on the R-group can be a group containing an acid chloride function. The $R^{4'}$ precursor groups can be deprotected and/or completed after the trimeric product is formed. The procedure is explained in detail in the following and involves the following steps:

1) functionalization of the iodinated isophtalic amine compound starting material's carboxylic acid groups into acid chlorides as intermediates using traditional methods
2) the compound from step 1) is reacted in dimethyl acetamide at elevated temperature to form non-ionic hydrophilic moiety such as amides moieties of formula (IV). Steps 1 and 2 here correspond to steps a) to c) in the procedure for production of the compound of formula (III) below.

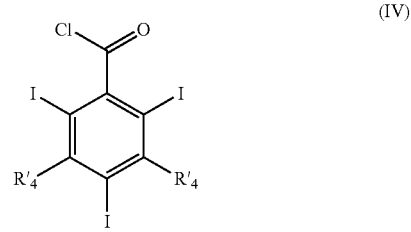

wherein $R^{4'}$ denotes a precursor of $R^4$ such as a acid chloride, an allylated amide group or an acylated amino group
3) The procedure described in (*Eur. J. Org. Chem.;* 2004, vol. 11, pp 2367-2364) is used to synthesise the (2,5)-4-(2-Carboxy-vinyl)-hepta-2,5-dienedioic acid
4) The triacid chloride is formed using traditional methods form the compound in step 3).
5) The compounds from steps 3) and 4) are combined in N,N-dimethylacetamide and reacted at ambient temperature to form compounds of formula (I)
6) if necessary, hydrolysis of $R^{4'}$ protected groups obtained from step 5) such as esters using traditional deacetylation methods to produce the compound of formula (I).

The general procedure can also be illustrated by the scheme below, where a compound of formula (III) is produced:

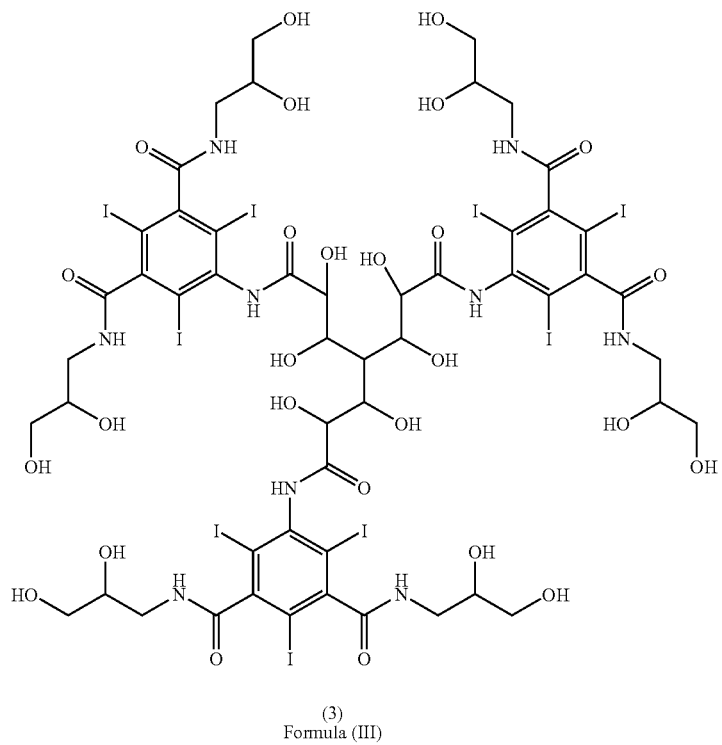

(3)
Formula (III)

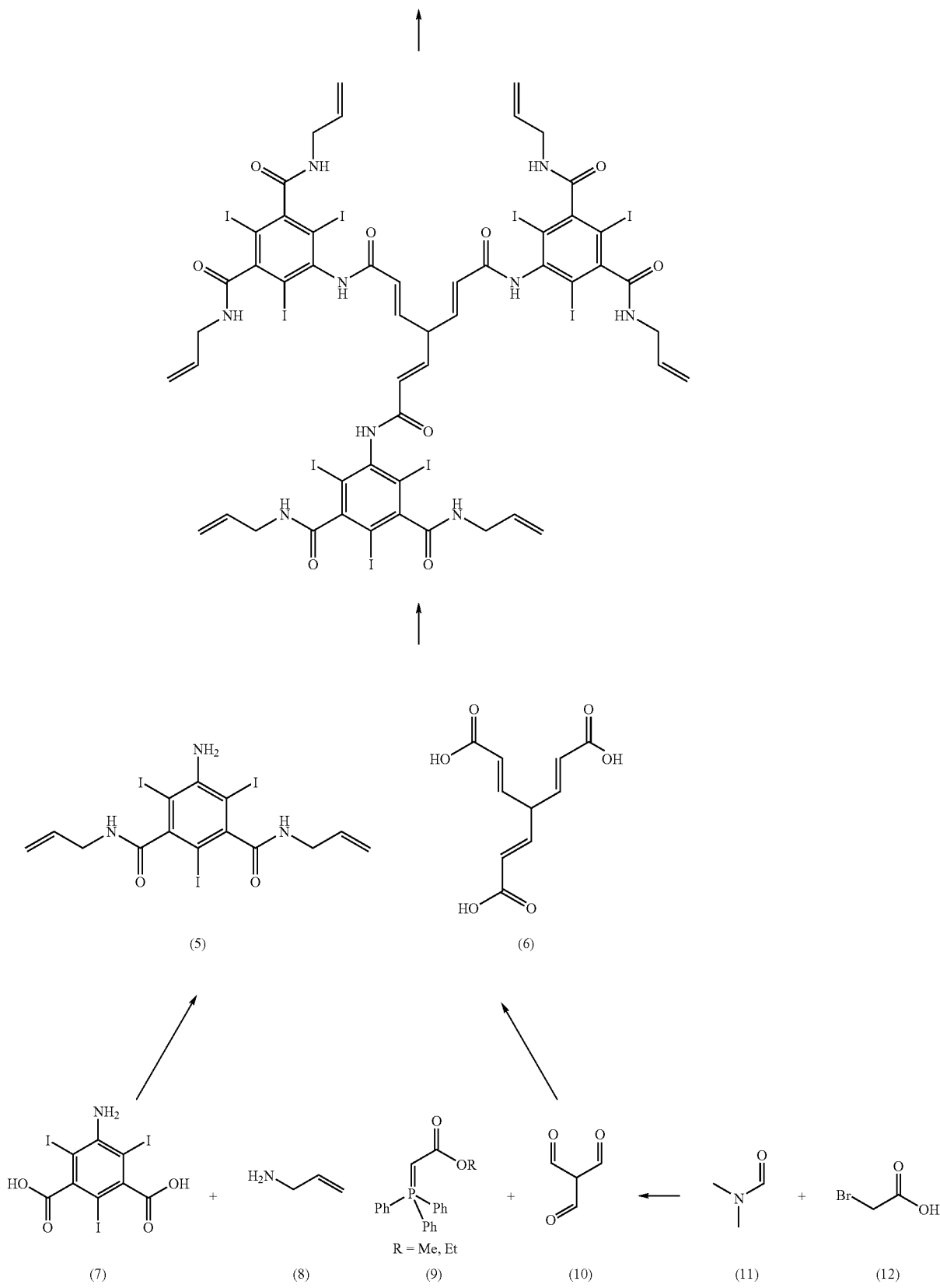

EXAMPLE

N,N'-Bis-(2,3-dihydroxy-propyl)-5-((2E,5E)-6-[3-N,N'-bis(2,3-dihydroxy-propylisophthalamide)-2,4,6-triiodo-phenylcarbamoyl]-4-{(E)-2-[3-N,N'-bis(2,3-dihydroxy-propylisophthalamide)-2,4,6-triiodo-phenylcarbamoyl]-vinyl}-hexa-2,5-dienoylamino)-2,4,6isophthalamide (Compound of formula (III))

a) Preparation of 5-Amino-2,4,6-triiodo-isophthaloyl dichloride

5-Amino-2,4,6-triiodo-isophtalic acid (30 g, 0.054 mol), thionyl chloride (8.2 ml, 0.113 mol) and pyridine (0.2 ml) in 1,2 dichloroethane (20 ml) were heated to 70° C. A portion of thionyl chloride (15.2 ml, 0.21 mol) was added dropwise during 1½ to 2 hrs, and the mixture was heated to 85° C. for 6 hrs. After cooling the reaction mixture to room temperature, it was poured into 300 g of ice-water. The yellow precipitate that formed was filtered off, sucked dry and then washed with water until washings showed a pH of ca 5. The filter cake was then dried in a vacuum oven at 50° C. for 3 hrs. A light yellow powder was obtained 31 g (~quant.) as the desired product.

$^{13}$C NMR (DMSOd$_6$) 66, 78.4, 148.9, 149.2, 169
MS (ES-) found 593.5 [M-H+], expected 593.7 b) Preparation of N,N'-Diallyl-5-amino-2,4,6-triiodo-isophthalamide

To a solution of 5-Amino-2,4,6-triiodo-isophthaloyl dichloride in dichloromethane was added allylamine (4 equivalents) under a nitrogen atmosphere at ambient temperature. The reaction was stirred for 18 hours. This yielded a precipitate which was found to be the desired product. $^1$H NMR (DMSOd$_6$) 8.62 (2H, t, j 4.5 Hz), 5.90 (2H, m), 5.46 (2H, br s), 5.37 (2H, d, j 9 Hz), 5.14 (2H, d, 6 Hz), 3.84 (4H, t, 3 Hz). $^{13}$C (DMSOd$_6$) 169.6, 149.0, 147.4, 116.0, 79.7, 41.5.

c) Preparation of Triformylmethane

The procedure described in (*Eur. J. Org. Chem.*; 2004, vol. 11 pp 2367-2364) was followed.

POCl$_3$ (13.8 mL 0.147 mol) was added dropwise to a cooled solution of DMF (C$_3$H$_7$NO, 40 mL, 0.518 mol, at about 0° C.) over a period of 1 h keeping the temperature below 5° C. during the addition. The solution initially appeared greenish but turned pale orange by the end of the addition. Then the ice-bath was removed and the dense mixture was stirred at room temperature for 1 h. Bromoacetic acid (7.15 g, 0.051 mol) was added in portions, and the mixture was heated for 24 h at 70° C. The brownish mixture was decomposed with ice/water (200 mL) and solid Na$_2$CO$_3$ was carefully added in large excess until pH 8. Absolute ethanol was added (2 L), and the inorganic salts were filtered off. The organic filtrate was evaporated slowly under a stream of air, and the pale yellowish residue was neutralized with H2SO4 (50%, 10 mL), extracted with CHCl$_3$ (3×200 mL) and dried over MgSO$_4$. After solvent removal, triformylmethane was obtained as yellowish crystals that were further purified by sublimation (2.3 g, yield 45% based on bromoacetic acid). The infrared data and elemental analysis have not been reported previously.

M.p. 102-103° C. (ref. M.p, 101° C.). FT-IR (KBr): v¯ 2828 (w, vC—H), 2731 (m, vC—H), 1699 (s, C=O), 1599(s), 1566 (s), 1561 (m), 1207 (s), 1166 (m), 826 (s), 723 (m) cm$^{-1}$.
C$_4$H$_4$O$_3$ (100.07): calcd. C, 48.01; H, 4.03. found C, 48.25; H, 4.11.

d) Preparation of (2,5)-4-(2-Carboxy-vinyl)-hepta-2,5-dienedioic acid

A mixture of triformylmethane and (triphenyl-lambda*5*-phosphanylidene)-acetic acid methyl or ethyl ester (5 equivalents) (Aldrich) will be heated in toluene. This will form (2,5)-4-(2-Methoxycarbonyl-vinyl)-hepta-2,5-dienedioic acid dimethyl ester (or its ethyl analogue). This will be purified by silica gel chromatography. The trimester will be hydrolised with aqueous sodium hydroxide to yield (2,5)-4-(2-Carboxy-vinyl)-hepta-2,5-dienedioic acid.

e) Preparation of (2,5)-4-(2-Chlorocarbonyl-vinyl)-hepta-2,5-dienedioyl dichloride To a solution of (2,5)-4-(2-carboxy-vinyl)-hepta-2,5-dienedioic acid in dichloromethane will be added thionyl chloride (15 equivalents) at ambient temperature. The mixture will be heated at reflux for up to 18 hours. The excess thionyl chloride will be removed at reduced pressure to yield (2,5)-4-(2-chlorocarbonyl-vinyl)-hepta-2,5-dienedioyl dichloride. This will be used without further purification.

f) Preparation of N,N'-Diallyl-5-{(2E,5E)-6-(3-N,N'-diallylisophthalamide-2,4,6-triiodo-phenylcarbamoyl)-4-[(E)-2-(3-N,N'-diallylisophthalamide-2,4,6-triiodo-phenylcarbamoyl)-vinyl]-hexa-2,5-dienoylamino}-2,4,6-triiodo-isophthalamide To a solution of N,N'-diallyl-5-amino-2,4,6-triiodo-isophthalamide in N,N-dimethylacetamide will be added (2,5)-4-(2-Chlorocarbonyl-vinyl)-hepta-2,5-dienedioyl dichloride (0.3 equivalents) and triethylamine (1 equivalent) at ambient temperature under a nitrogen atmosphere. The mixture will be stirred at ambient temperature for up to 24 hours. The solvent will be removed at reduced pressure and the crude mixture will be purified using silica gel chromatography to yield the desired trimer.

g) Preparation of N,N'-Bis-(2,3-dihydroxy-propyl)-5-((2E,5E)-6-[3-N,N'-bis(2,3-dihydroxy-propylisophthalamide)-2,4,6-triiodo-phenylcarbamoyl]-4-{(E)-2-[3-N,N'-bis(2,3-dihydroxy-propylisophthalamide)-2,4,6-triiodo-phenylcarbamoyl]-vinyl}-hexa-2,5-dienoylamino)-2,4,6 isophthalamide To a solution of N,N'-Diallyl-5-{(2E,5E)-6-(3-N,N'-diallylisophthalamide-2,4,6-triiodo-phenylcarbamoyl)-4-[(E)-2-(3-N,N'-diallylisophthalamide-2,4,6-triiodo-phenylcarbamoyl)-vinyl]-hexa-2,5-dienoylamino}-2,4,6-triiodo-isophthalamide dissolved in a mixture of acetone/water (9/1) will be added a solution of osmium catalyst (OsO$_4$, t-BuOH and a few drops of t-BuOOH) followed by addition of N-methylmorpholine oxide. The mixture will be stirred over night at ambient temperature. After quenching the reaction with a 10 ml solution of sodium hydrogen sulphite (15%) the mixture will be evaporated to dryness. The crude will be purified via HPLC.

The invention claimed is:

1. Compounds of formula (I)

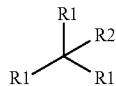

Formula (I)

and salts or optical active isomers thereof,
wherein
each $R^1$ independently are the same or different and denote a moiety —CHOH—CHOH—CO—$NR^3$—R;
$R^2$ denotes hydrogen or a $C_1$-$C_4$ alkyl where the alkyl group may be substituted by hydroxyl and amino groups and interrupted by an oxygen atom;
each $R^3$ independently are the same or different and denote a hydrogen atom or an acyl group;
each R independently are the same or different and denote a triiodinated phenyl group, preferably a 2,4,6-triiodinated phenyl group further substituted by two groups $R^4$ wherein each $R^4$ are the same or different and denote a hydrogen atom or a non-ionic hydrophilic moiety, provided that at least one $R^4$ group in the compound of formula (I) is a hydrophilic moiety.

2. Compound as claimed in claim 1 wherein $R^2$ is a hydrogen atom or a methyl group.

3. Compound as claimed in claim 2 wherein $R^2$ denotes a hydrogen atom.

4. Compound as claimed in claim 1, wherein all $R^3$ denotes hydrogen atoms.

5. Compound as claimed in claim 1 wherein each R are the same or different and denote a 2,4,6 triiodinated phenyl group, further substituted by two groups $R^4$.

6. Compounds as claimed in claim 5 wherein each $R^4$ are the same or different and denote a non-ionic hydrophilic moiety comprising esters, amides or amine moieties, optionally further substituted by a straight chain or branched chain $C_{1-10}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

7. Compounds as claimed in claim 6 wherein $R^4$ are the same or different and denote a non-ionic hydrophilic moiety comprising esters, amides or amine moieties, optionally further substituted by a straight chain or branched chain $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

8. Compounds as claimed in claim 7 wherein $R^4$ are the same or different and denote a non-ionic hydrophilic moiety comprising esters, amides or amine moieties, further substituted by a straight chain or branched chain $C_{1-5}$ alkyl groups substituted by 1 to 3 hydroxy groups.

9. Compounds as claimed in claim 8 wherein each $R^4$ are the same or different and are polyhydroxy $C_{1-5}$ alkyl, hydroxyalkoxyalkyl with 1 to 5 carbon atoms or hydroxypolyalkoxyalkyl with 1 to 5 carbon atoms attached to the iodinated phenyl group via an amide or carbamoyl linkage.

10. Compounds as claimed in claim 9 wherein each $R^4$ are the same or different and are selected from the groups of the formulas —CONH—$CH_2$—$CH_2$OH
—CONH—$CH_2$—CHOH—$CH_2$OH
—CON($CH_3$)$CH_2$—CHOH—$CH_2$OH
—CONH—CH—($CH_2$OH)$_2$
—CON—($CH_2$—$CH_2$OH)$_2$
—CON—($CH_2$—CHOH—$CH_2$OH)$_2$
—$CONH_2$
—$CONHCH_3$
—NHCOCH$_2$OH
—N(COCH$_3$)H
—N(COCH$_3$)$C_{1-3}$ alkyl
—N(COCH$_3$)-mono, bis or tris-hydroxy $C_{1-4}$ alkyl
—N(COCH$_2$OH)-hydrogen, mono, bis or tris-hydroxy $C_{1-4}$ alkyl
—N(CO—CHOH—$CH_2$OH)-hydrogen, mono, bis or tri-hydroxylated $C_{1-4}$ alkyl
—N(CO—CHOH—CHOH—$CH_2$OH)-hydrogen, mono, bis or trihydroxylated $C_{1-4}$ alkyl
—N(COCH$_2$OH)$_2$
—CON($CH_2$—CHOH—$CH_2$—OH)($CH_2$—$CH_2$OH)
—CONH—C($CH_2$OH)$_3$
—CONH—CH($CH_2$—OH)(CHOH—$CH_2$OH).

11. Compounds as claimed in claim 10 wherein each $R^4$ are the same or different and are selected from the groups of the formulas —CONH—$CH_2$—CHOH—$CH_2$OH, —CONH—CH—($CH_2$OH)$_2$, —CON—($CH_2$—$CH_2$OH)$_2$, —CON($CH_2$—CHOH—$CH_2$OH)$_2$, —CON($CH_3$)$CH_2$—CHOH—$CH_2$OH, —NHCOCH$_2$OH and —N(COCH$_2$OH)-mono, bis or tris-hydroxy $C_{1-4}$ alkyl.

12. Compound as claimed in claim 11 wherein each $R^4$ are equal.

13. Compound as claimed in claim 12 wherein each $R^4$ denotes —CO—NH—$CH_2$—CHOH—$CH_2$OH.

14. Compound as claimed in claim 1 being N,N'-Bis-(2,3-dihydroxy-propyl)-5-((2E,5E)-6-[3-N,N'-bis(2,3-dihydroxy-propylisophthalamide)-2,4,6-triiodo-phenylcarbamoyl]-4-{(E)-2-[3-N,N'-bis(2,3-dihydroxy-propylisophthalamide)-2,4,6-triiodo-phenylcarbamoyl]-vinyl}-hexa-2,5-dienoylamino)-2,4,6-isophthalamide.

15. A diagnostic agent comprising a compound of formula (I) as defined in claim 1.

16. A diagnostic composition comprising a compound of formula (I) as defined in claim 1 together with a pharmaceutically acceptable carrier or excipient.

17. An X-ray diagnostic composition comprising a compound of formula (I) as defined in claim 1 together with a pharmaceutically acceptable carrier or excipient.

18. A method of diagnosis comprising administration of compounds of formula (I) as defined in claim 1 to the human or animal body, examining the body with a diagnostic device and compiling data from the examination.

19. A method of imaging, specifically X-ray imaging, comprising administration of compounds of formula (I) as defined in claim 1 to the human or animal body, examining the body with a diagnostic device and compiling data from the examination and optionally analysing the data.

20. Compound as claimed in claim 1 wherein each $R^3$ denotes a hydrogen atom or a $C_2$ to $C_5$ aliphatic organic acid residue.

21. Compound as claimed in claim 20 wherein the $C_2$ to $C_5$ organic acid residues are selected from the group of acetyl, propionyl, butyryl, isobutyryl and valeriyl residues.

22. Compound as claimed in claim 20 wherein each $R^3$ denotes hydrogen atoms or acetyl groups.

* * * * *